United States Patent
Brine, III et al.

(10) Patent No.: US 8,220,069 B2
(45) Date of Patent: Jul. 17, 2012

(54) EYE PROTECTOR

(75) Inventors: William H. Brine, III, Hopkinton, MA (US); Jonathan Baker, Thornton, NH (US); Eric Darnell, South Strafford, VT (US); Steve Moore, Liverpool, NY (US); Joel Robinson, Oswego, NY (US); C. Graham Tuttle, Liverpool, NY (US)

(73) Assignee: Sport Helmets, Inc.

( * ) Notice: Subject to any disclaimer, the term of this patent is extended or adjusted under 35 U.S.C. 154(b) by 0 days.

(21) Appl. No.: 12/585,908

(22) Filed: Sep. 29, 2009

(65) Prior Publication Data

US 2011/0072549 A1 Mar. 31, 2011

(51) Int. Cl.
*A41D 13/00* (2006.01)
(52) U.S. Cl. .............................................................. 2/9
(58) Field of Classification Search .................. None
See application file for complete search history.

(56) References Cited

U.S. PATENT DOCUMENTS

| | | | | |
|---|---|---|---|---|
| 1,843,585 | A * | 2/1932 | Van Orman | 2/9 |
| 6,598,234 | B1 * | 7/2003 | Brown et al. | 2/9 |
| 6,708,339 | B1 * | 3/2004 | Smith, Jr. | 2/9 |
| 7,430,763 | B1 * | 10/2008 | Santos | 2/9 |
| 7,434,268 | B2 * | 10/2008 | Futch | 2/9 |
| 2007/0266471 | A1 * | 11/2007 | Lin | 2/9 |
| 2009/0178185 | A1 * | 7/2009 | Brine et al. | 2/424 |

* cited by examiner

*Primary Examiner* — Katherine Moran
(74) *Attorney, Agent, or Firm* — H. Jay Spiegel

(57) ABSTRACT

Embodiments of an eye protector are made of a molded plastic part connected with a metal part. The plastic part consists of a generally C-shaped configuration with an elongated portion overlying the eyebrows and arcuate fingers designed to overlie the wearer's cheekbones. The metallic part includes an arcuate portion staggered significantly forwardly with respect to the plastic part. The horizontal stagger virtually precludes a ball from impacting on both the plastic part and the metallic part simultaneously, and the thin profile of the metallic part causes deflection of a ball rather than rebound. Embodiments also include a downwardly depending inverted V-shaped portion that protects the wearer's face below the eyes.

24 Claims, 17 Drawing Sheets

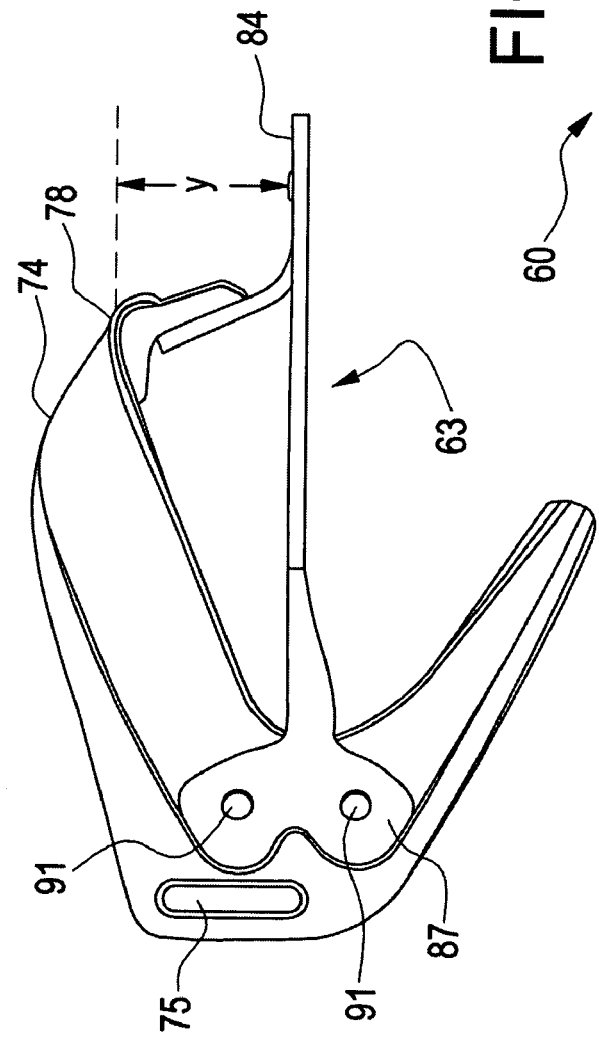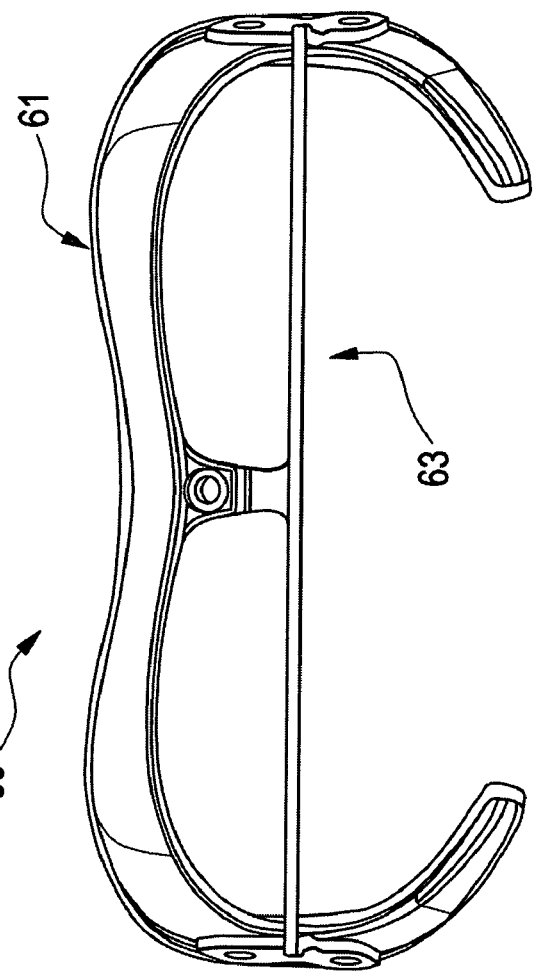

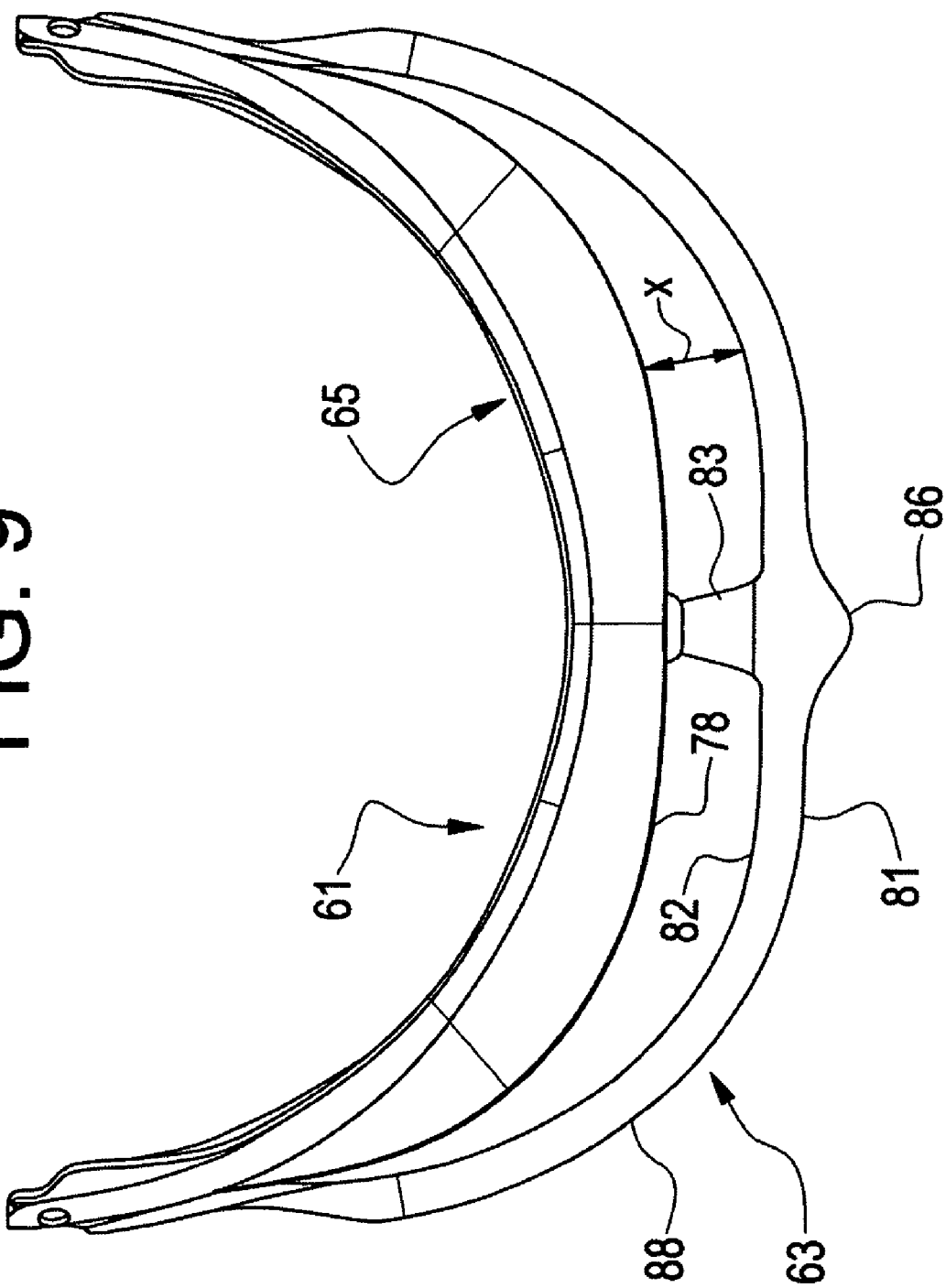

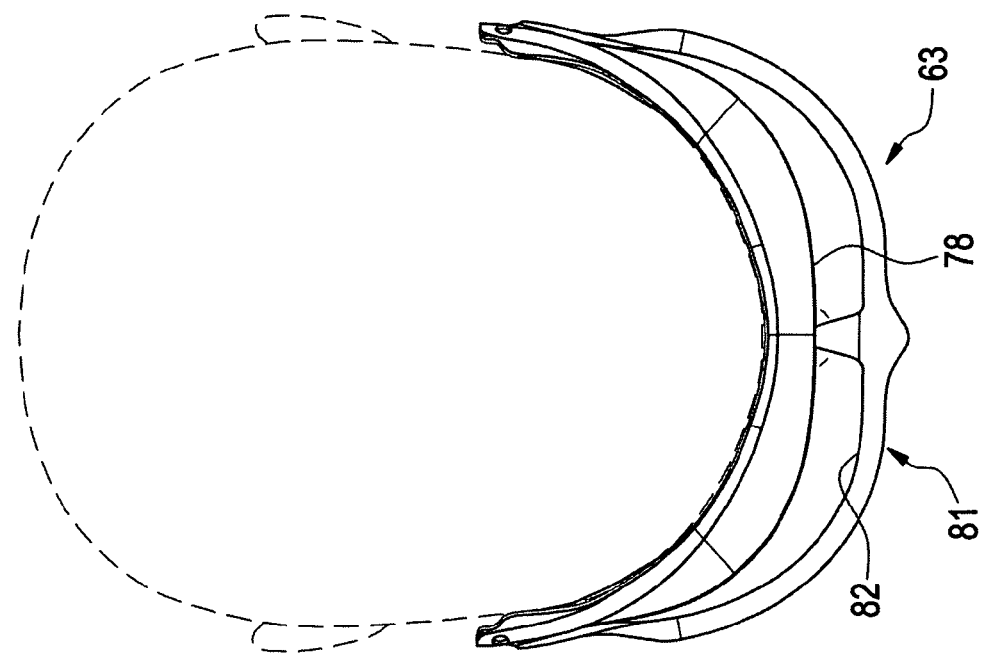
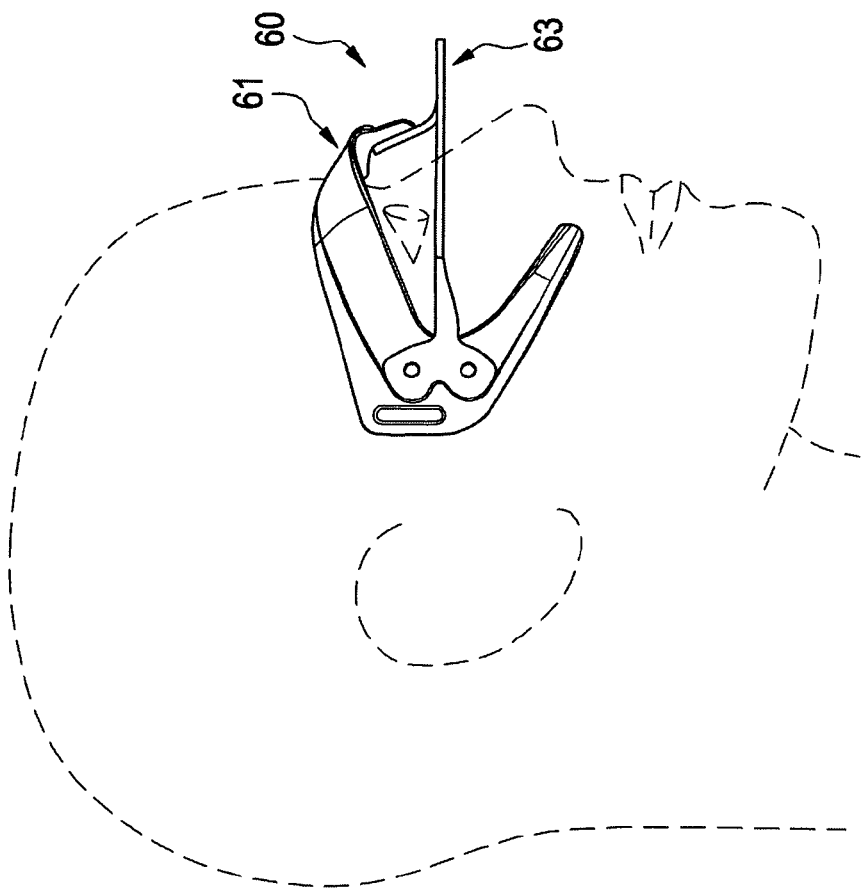

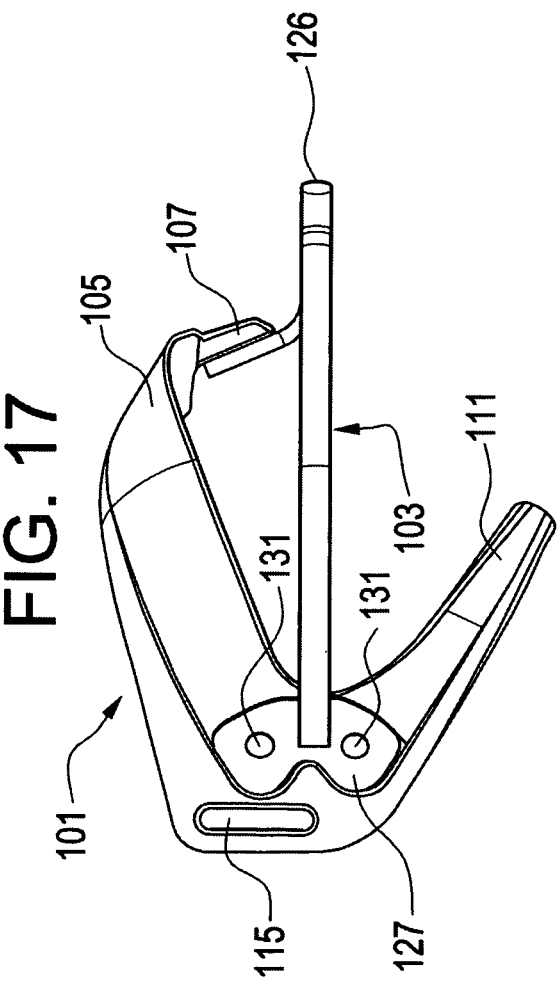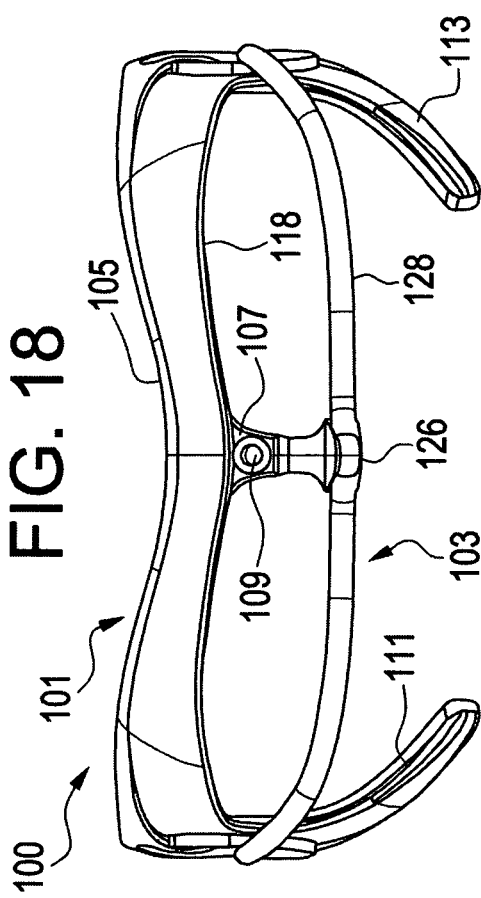

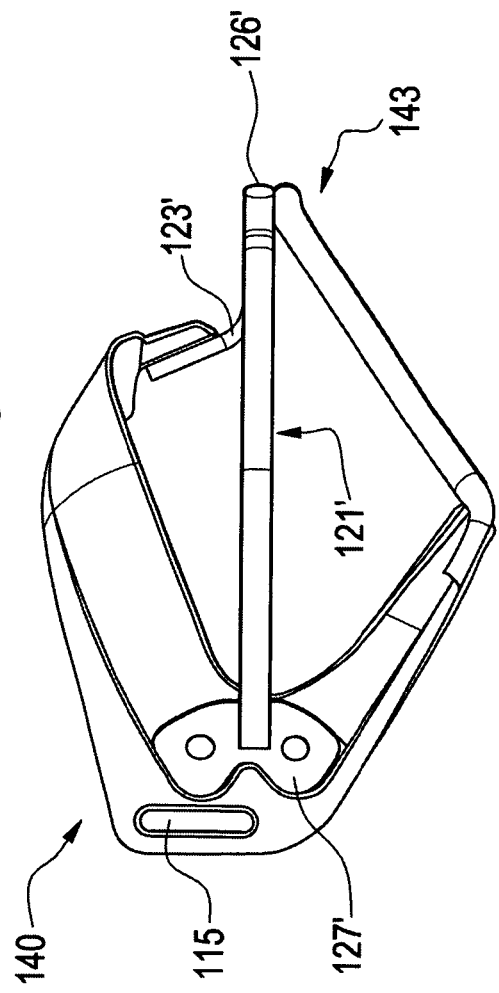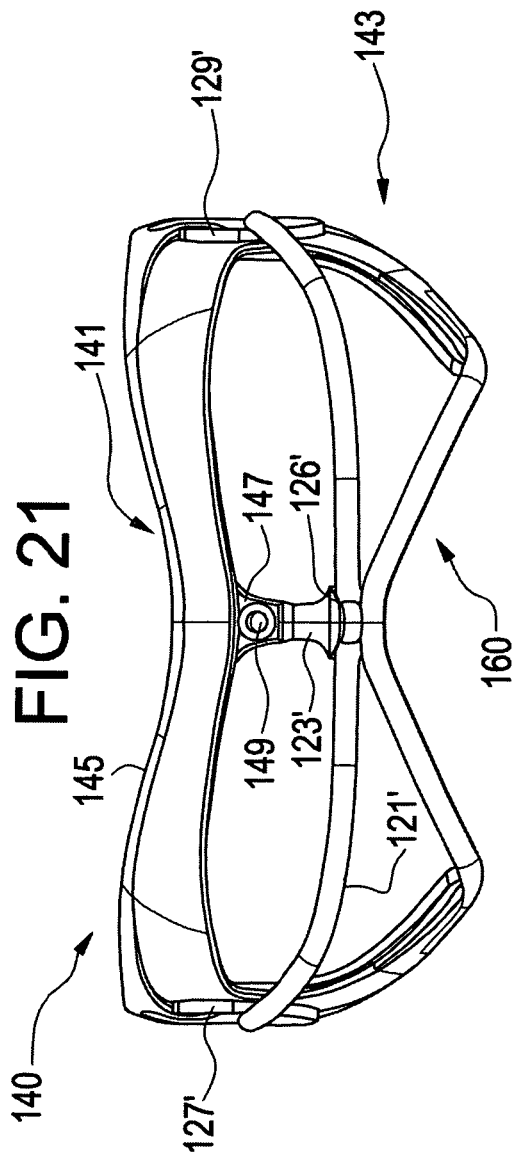

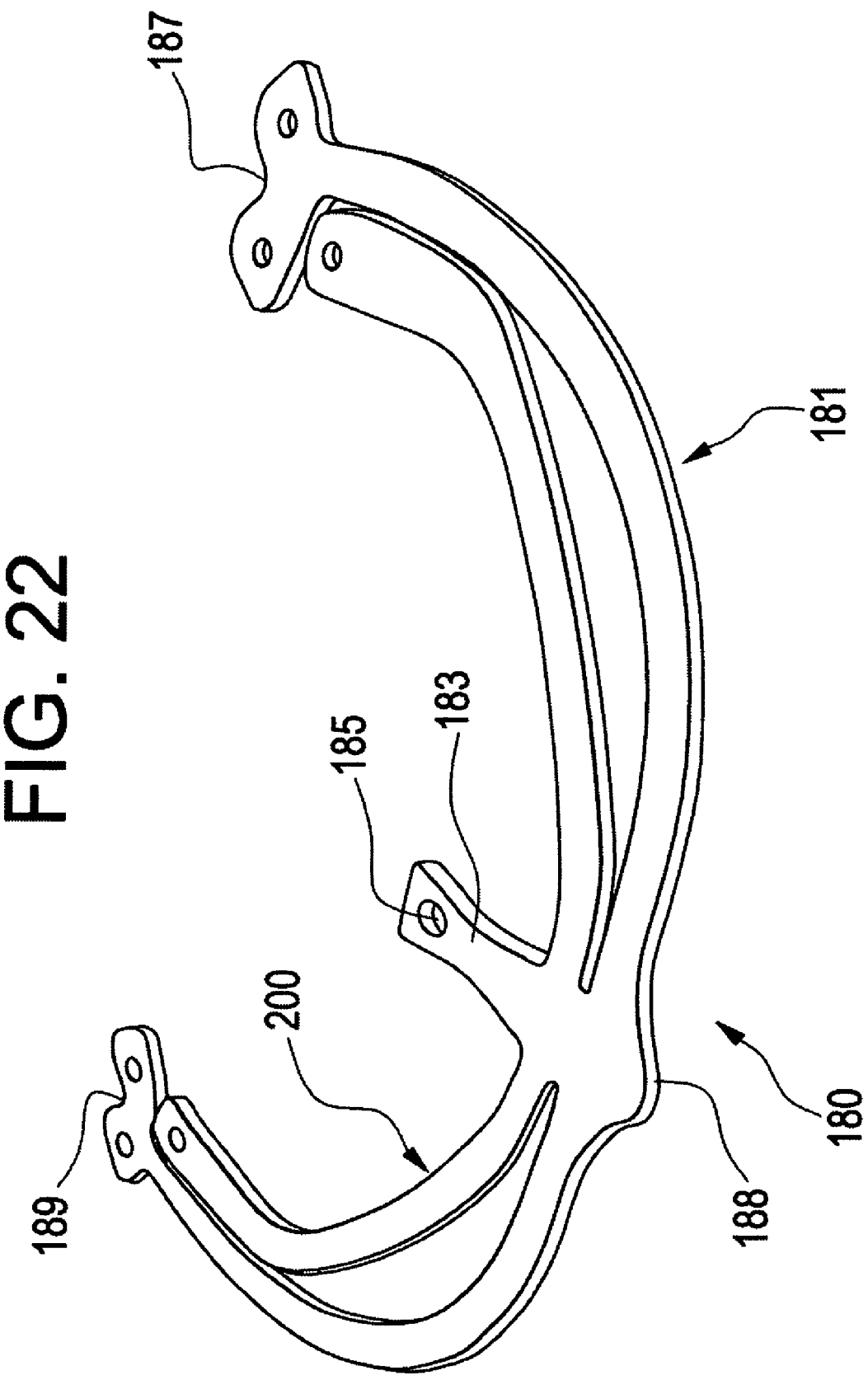

EYE PROTECTOR

BACKGROUND OF THE INVENTION

The present invention relates to embodiments of an improved eye protector, particularly designed for the game of women's lacrosse. In men's lacrosse, players are protected by a helmet completely covering the head and including a protective cage and a chin guard. By contrast, in the game of women's lacrosse, no such headgear is worn. The only protection worn by women playing the game of lacrosse consists of eye protection.

Eye protectors currently on the market are typically designed to provide a blocking function. That is, they are configured so that a lacrosse ball coming toward the eye protector is blocked from hitting the eyes of the wearer in such a way that the ball typically bounces back toward its point of origin. When this occurs, the force of the incoming ball is transferred to the wearer's face via the eye protector and a maximum amount of force is transferred to the wearer's face. Present day eye protectors designed for the game of women's lacrosse are less concerned with player visibility than they are concerned with eye protection. Such eye protectors typically include a plurality of vertically disposed support bars that provide structural integrity for the eye protector but, at the same time, block the vision of the wearer and, in fact, perform a distraction function, distracting the wearer from occurrences during a lacrosse game.

Applicants' Assignee, Sport Helmets, Inc., trading as Cascade (Cascade), sells an eye protector that is depicted in FIGS. 1 and 2. The eye protector 10 includes a central vertical bar 11 separating openings 13 and 15 for the eyes of the wearer. Additional vertical bars 17 and 19 provide structural support and also define sides of additional openings 21 and 23.

As shown in FIG. 1, the opening 13 is defined by an upper bar 25 and a lower bar 27, while the opening 15 is defined by an upper bar 29 and a lower bar 31. With reference to FIG. 2, it is seen that the lower bars 27 and 31 protrude forwardly a slight distance in front of the upper bars 25 and 29. The vertical bar 11 also protrudes forwardly of the openings 13 and 15. The forward stagger of the lower bars 27, 31 with respect to the upper bars 25 and 29 is extremely slight, and the result is that for most ball impacts, the eye protector 10 performs a blocking function, repelling the ball back toward its source.

With reference to FIGS. 3 and 4, another eye protector for women's lacrosse is made by DeBeer. The DeBeer protector 40 includes a plastic portion 41 to which is attached a metal portion 43 made of rectangular cross-section wire. As seen in particular in FIG. 3, the eye openings are designated by the reference numerals 45 and 47. Vertical angled bars 49 and 51 support the upper bars 48 and 50, defining the upper extents of the eye openings 45 and 47. The bars 49 and 51 attach to horizontal bar 53 that facilitates attachment to the member 41. Lower bars 55, 57 define the lower extent of the eye openings 45 and 47. Another vertical bar 52 separates and defines the eye openings 45 and 47. As seen in FIG. 4, the bars 49 and 51 extend forwardly of the bar 53, and the bars 48, 50 are directly over the bars 55 and 57, respectively. Thus, the bars 45, 50 and 55, 57 are equidistant in front of the eyeballs of the wearer. This makes it more likely that incoming balls will be blocked back toward their source as compared to deflecting away.

A regulation lacrosse ball is about 2.47 to 2.55 inches in diameter and weighs from 5 to 5.25 ounces. As shown in FIG. 5, when a lacrosse ball B is thrown or shot at a high rate of speed, it tends to elongate into the shape of an ovoid upon impact. When this occurs, a diameter reduces below 2.47 inches. This phenomenon must be taken into account when designing the dimensions of eye protectors to preclude a ball from intruding past horizontal bars of an eye protector and impact the eyeball. This possibility must be precluded at all costs.

Applicants have found that an eye protector for women's lacrosse provides superior protection for the eyes of the wearer if it is designed to facilitate deflection of a lacrosse ball away from the wearer's eyes rather than accomplishing a pure blocking function. Eye protectors in which the upper and lower bars surrounding the eyes are generally equidistantly spaced from the wearer's head are less likely to deflect the ball but, rather, are more likely to block the ball and send it on a path in the general direction of its source. When this occurs, maximum force is transferred to the wearer's head. If an eye protector could be designed that deflects the lacrosse ball rather than directly repelling it, forces imposed on the wearer's head will be significantly reduced and protection to the wearer's eyeballs will necessarily be enhanced. It is with these thoughts in mind that the present invention was developed.

SUMMARY OF THE INVENTION

The present invention relates to embodiments of an eye protector. The present invention includes the following interrelated objects, aspects and features:

(1) In a first aspect, the present invention contemplates an eye protector made of a molded plastic part connected with a part created out of a thin sheet of metal stock material. The plastic part consists of a generally C-shaped configuration with an elongated portion overlying the eyebrows and at the opposite ends of the elongated portion, arcuate fingers curving toward one another and designed to overlie the cheekbones of the wearer. At the center of the elongated portion, a downwardly depending nib is provided including an opening to facilitate attachment with the metallic part.

(2) A first embodiment of the metallic part is preferably cut out of a flat thin sheet of metallic stock material such as, for example, aluminum. The metallic portion includes an arcuate portion staggered significantly forwardly with respect to the plastic part and having a central tab bent upwardly and having an opening aligned with the opening in the downwardly depending nib of the plastic part so that a rivet or other fastener may fasten the metallic part to the plastic part at that location.

(3) Aligned with the central tab is a forwardly extending nose bump for a purpose to be described in greater detail hereinafter. At the lateral terminations of the arcuate portion, wing-shaped attachment members are provided that facilitate attachment to lateral sides of the plastic part at the intersection between the elongated portion and the downwardly depending portions. The wing-shaped attachment members are formed with holes therethrough alignable with holes in the plastic part so that any desired fastening means such as, for example, rivets may be employed to securely fasten the wing-shaped portions to the plastic part.

(4) The stagger between the forward-most edge of the plastic part and the rear-most edge of the arcuate portion of the metallic part is in the order of ½ to ⅝ inch. The vertical spacing between the forward edge of the plastic part and the top surface of the arcuate portion of the metallic part is preferably about 1.1 inches, although a variation of up to 3/16 inches in either direction is acceptable. The stagger and vertical spacing are designed, not only to preclude ball impacts on the eyes and adjacent facial structures, but also with avoidance of blind spots in mind. Scotomas are blind spots created by an object that is proportionately too large in comparison to a person's pupil at a given distance. The thin profile of the metallic part contributes to prevention of Scotomas.

(5) In an important feature of the present invention, the sole vertical support between the metallic part and the plastic part is the centrally located downwardly depending nib on the plastic part and the upwardly extending central tab on the metallic part. This provides maximum visibility to the wearer with no other obstructions to vision.

(6) The forward stagger of the arcuate portion of the metallic part with respect to the curvature of the elongated portion of the plastic part is critical to the proper operation of the present invention. Applicants have found that most impacts on an eye protector worn by a lacrosse player either result from horizontal flight of the lacrosse ball or nearly horizontal flight. The horizontal stagger described above virtually precludes a ball from impacting on both the plastic part and the metallic part simultaneously. Moreover, the thin profile of the metallic part means that unless a lacrosse ball hits the metallic part precisely at its largest diameter, with equal portions of the ball above and below, the result will be deflection of the ball either over the head of the wearer or off to the side of the wearer. This effect significantly differs from what occurs in prior art eye protectors in which the lacrosse ball often impacts above and below the eye of the wearer simultaneously causing both a direct rebound and an imposition of greater force on the head of the wearer as a result. The thin profile is also defined by the cross-section of the metallic part which is relatively thin in its vertical dimension as compared to its horizontal direction. The ratio horizontal/vertical may be 2/1 to as much as 4/1 at the nose bump. The thin profile helps resist deformation of the metallic part when impacted, as compared to a situation in which the ratio might be closer to 1/1. Because the metallic part has a ratio horizontal/vertical of at least 2/1, when a force is applied on its forward facing edge, pushing inward from outside its arcuate shape, it will hold its shape and strongly resist deflection or collapse.

(7) The design of the edges and forward facing surface of the plastic part also facilitates deflection rather than rebound. As seen from the side, the curved surface of the plastic part subtends an angle with respect to the head of the wearer so that a ball striking the plastic part flush will be caused to deflect upwardly and over the head of the wearer. The fingers downwardly depending from the lateral sides of the curved portion of the plastic part preclude the inventive eye protector from rolling downwardly as a result of an impact. Upon impact, the fingers are engaging the cheeks of the wearer and act as a limit stop precluding pivoting movement.

(8) In a second embodiment of the present invention, the molded plastic part is the same as in the first embodiment. The metallic part instead of being fabricated from flat metallic stock material is manufactured from thin circular cross-section wire-like or tubular material. The thickness of the wire or tube corresponds to the thickness of the metal stock material from which the metallic part of the first embodiment is fabricated. This is the case to avoid Scotomas as explained above. For a tube or wire having a diameter corresponding to the height of a metallic part made of flat stock, for the same material, the metallic part made of flat stock is somewhat stronger and better able to resist deflection due to the minimum 2/1 ratio between its horizontal and vertical dimensions. Of course, other cross-sectional shapes for the metallic part may be employed.

(9) A third embodiment of the present invention is similar to the second embodiment, but adds the provision of an inverted V-shaped wire or tube portion that extends below the field of vision, and helps protect portions of the wearer's face below the eyes.

(10) A fourth embodiment is similar to the third embodiment, but the metallic part including the inverted V-shaped portion is made of a flat thin sheet of metallic stock material as is the case in the first embodiment.

Accordingly, it is a first object of the present invention to provide an improved eye protector.

It is a further object of the present invention to provide such an improved eye protector with a plastic molded part including a curved portion designed to overlie the eyebrows of the wearer and a metallic part made of flat stock in a first embodiment, and designed to define the lower-most surround of the eyes of the wearer.

It is a still further object of the present invention to provide such an eye protector in which the metallic part is significantly staggered forwardly of the curved portion of the metallic part to best facilitate deflection of incoming lacrosse balls rather than rebounding of them.

It is a still further object of the present invention to provide such an eye protector in which downwardly depending fingers incorporated in the plastic part preclude rolling downwardly of the eye protector on an impact from a lacrosse ball.

It is a yet further object of the present invention to provide such an eye protector in which the front surface of the curved portion of the plastic part is arranged at an angle to facilitate deflection of incoming lacrosse balls rather than rebounding thereof.

It is a yet further object of the present invention to provide such an eye protector in which in a second embodiment thereof, the metallic part is made of a thin wire having a thickness approximating the thickness of the metal stock from which the metallic part of the first embodiment is made.

It is a still further object of the present invention to provide such an eye protector in which in third and fourth embodiments thereof an additional inverted V-shaped part is incorporated in the metallic part to protect portions of the face below the eyes of the wearer.

These and other objects, aspects and features of the present invention will be better understood from the following detailed description of the preferred embodiment when read in conjunction with the appended drawing figures.

BRIEF DESCRIPTION OF THE DRAWINGS

FIG. 7 shows a side perspective view of the present invention.

FIG. 8 shows a front view of the present invention.

FIG. 9 shows a top view of the present invention.

FIG. 14 shows a view similar to that of FIG. 7, but showing the eye protector as worn by a wearer.

FIG. 15 shows a view similar to that of FIG. 9, but showing the inventive eye protector as worn by a wearer.

FIG. 17 shows a side view of the second embodiment of the present invention.

FIG. 18 shows a front view of the second embodiment of the present invention.

FIG. 20 shows a side view of the third embodiment of the present invention.

FIG. 21 shows a front view of the third embodiment of the present invention.

FIG. 22 shows a perspective view of the metallic part of a fourth embodiment of the present invention.

SPECIFIC DESCRIPTION OF THE PREFERRED EMBODIMENTS

Figure 1:
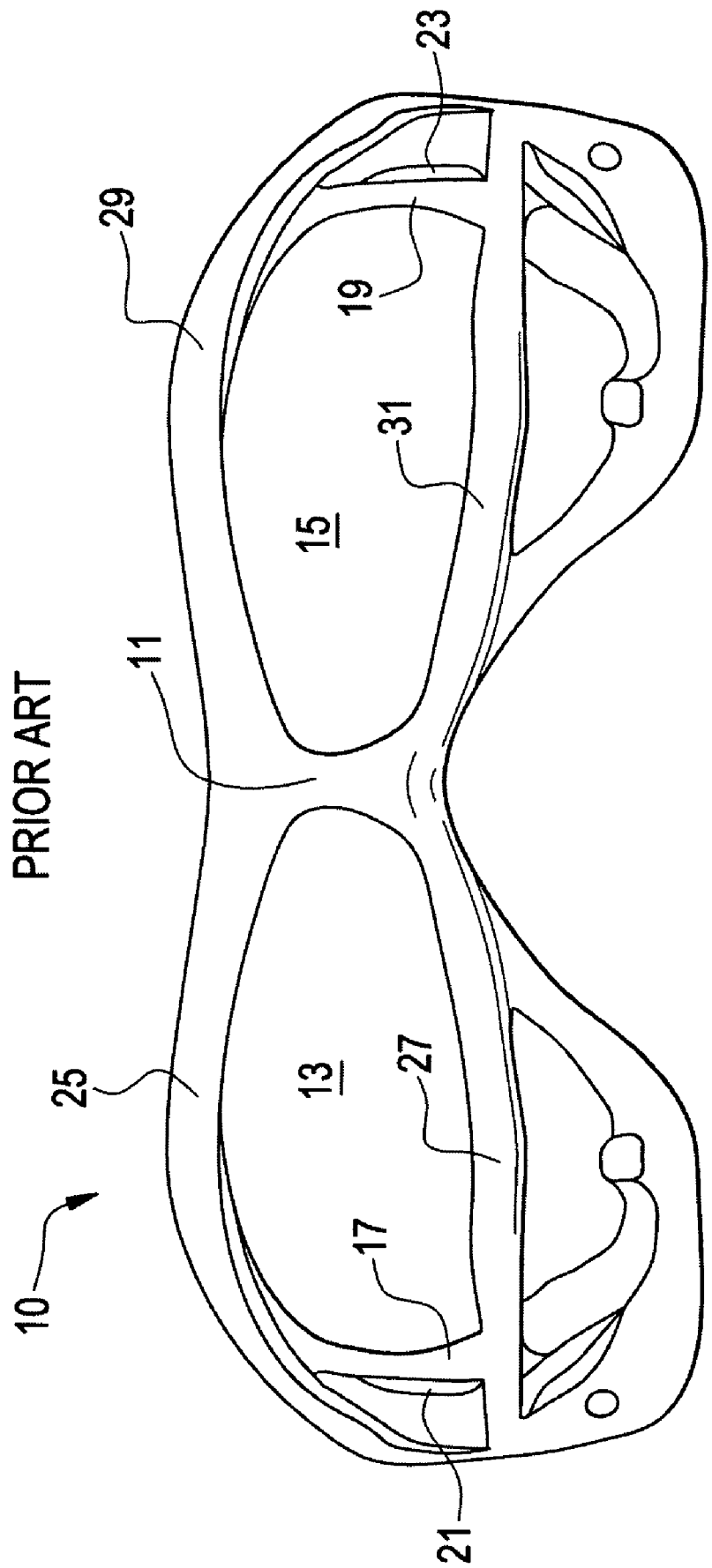
FIG. 1 shows a front view of a prior art eye protector manufactured and sold by Applicants' Assignee, Cascade.
Figure 2:
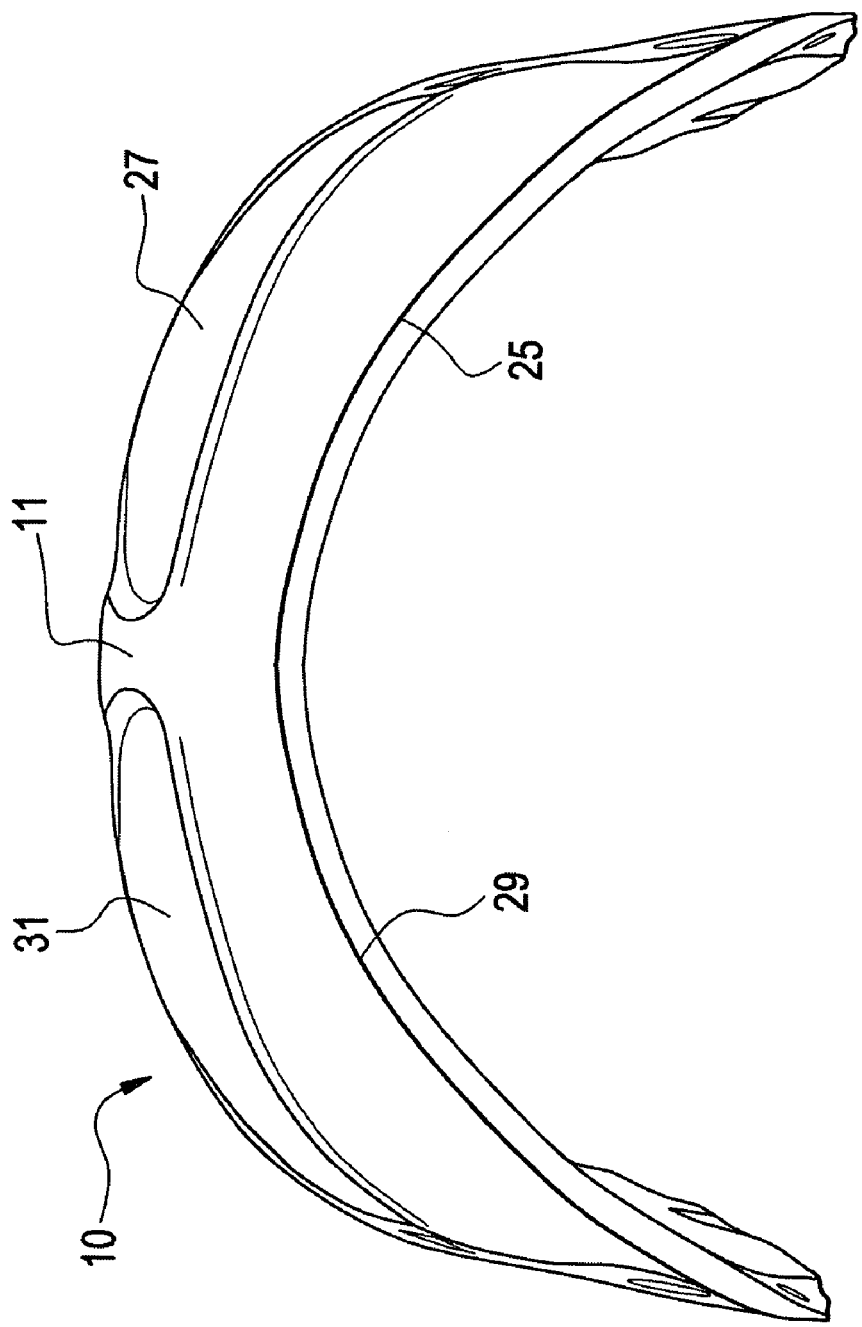
FIG. 2 shows a top view of the eye protector of FIG. 1.
Figure 3:
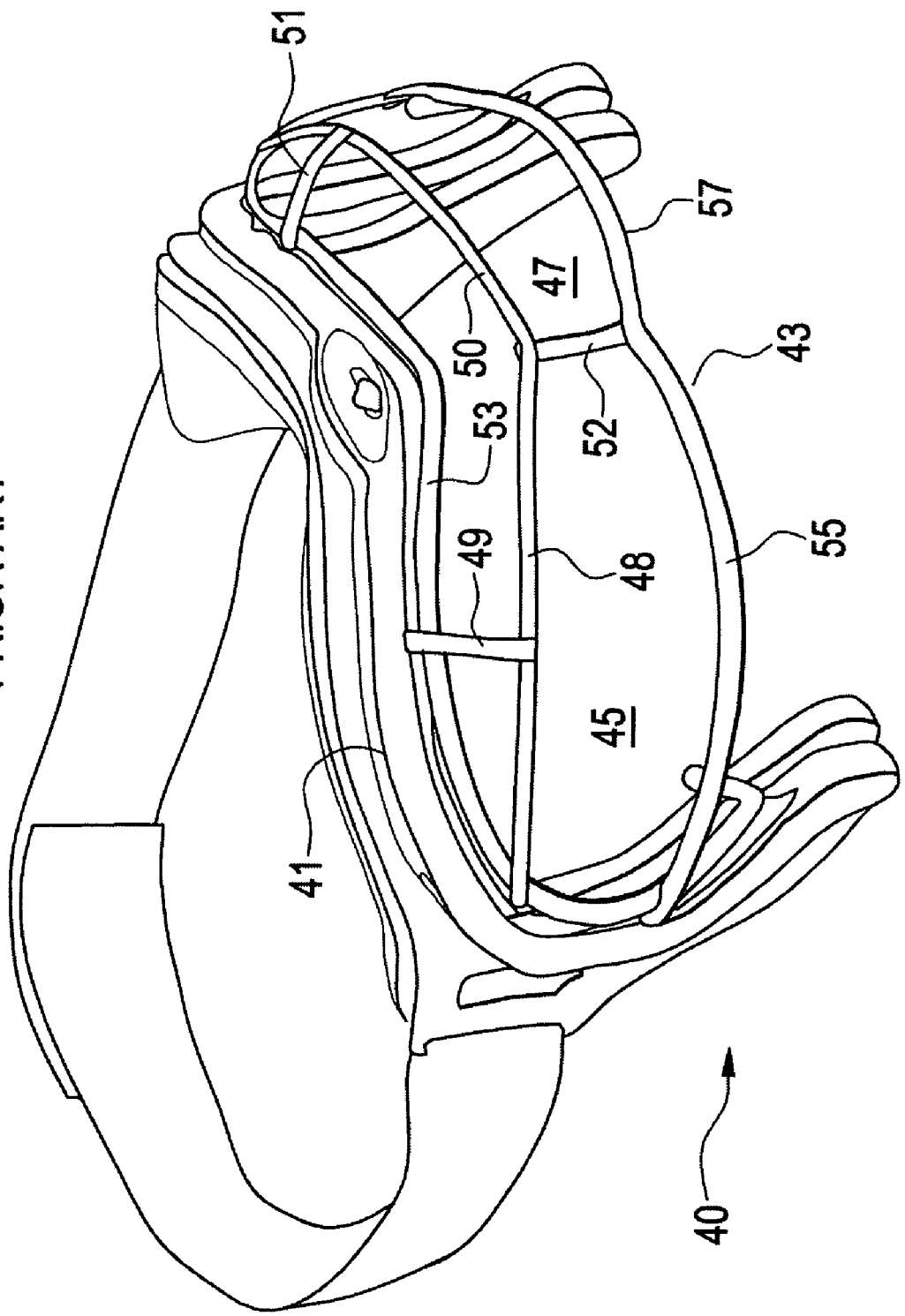
FIG. 3 shows a perspective view of an eye protector manufactured by DeBeer.
Figure 4:
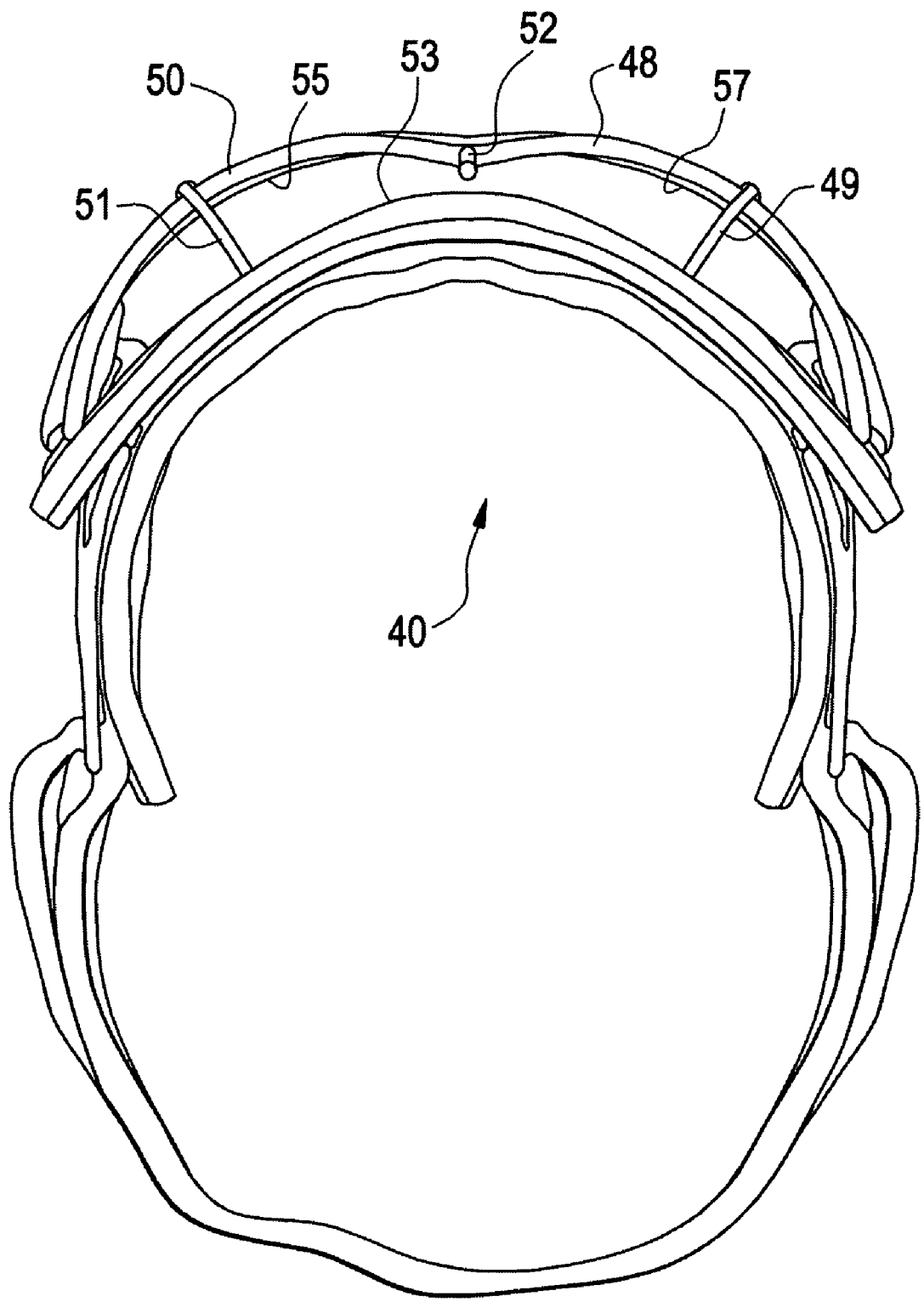
FIG. 4 shows a top view of the eye protector of FIG. 3.

Reference is first made to FIGS. 6-9. With reference to those figures, the first embodiment of the eye protector is generally designated by the reference numeral 60 which is seen to include a molded plastic part 61 and a fabricated metallic part 63.

Figure 12:
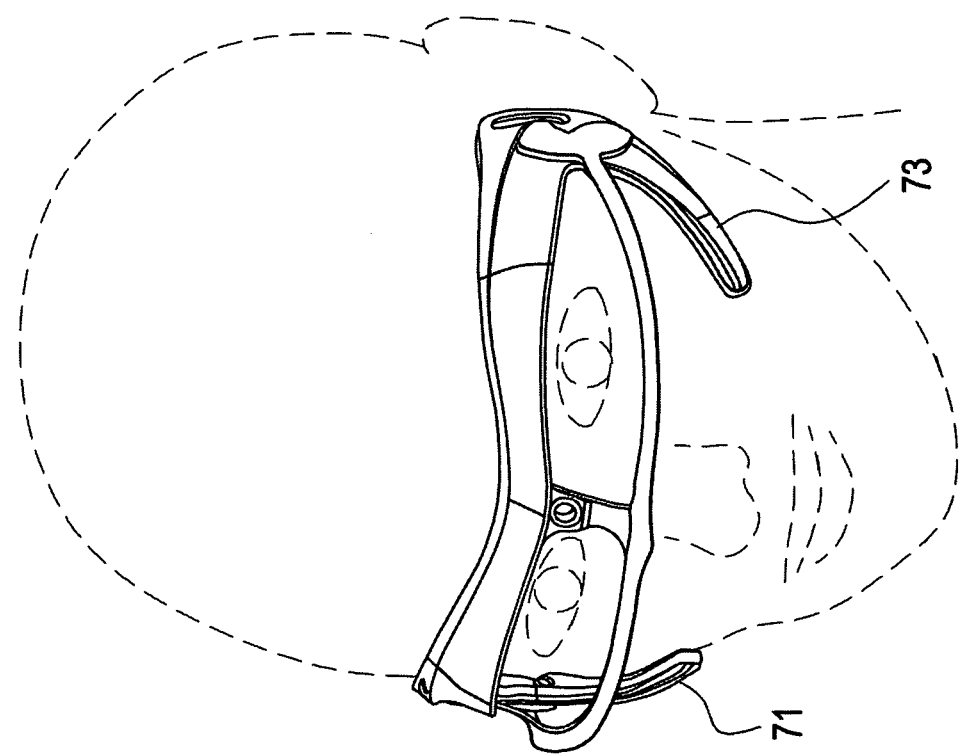
FIG. 12 is a view similar to that of FIG. 6, but showing the inventive eye protector as worn by a wearer.

The plastic part 61 includes a laterally elongated arcuate portion 65 that is configured to overlie the eyebrows of the wearer (see also FIG. 12) and curves rearwardly toward the ears of the wearer (FIG. 12).

Centrally located on the elongated portion 65 is a downwardly depending central tab 67 having an opening 69 therethrough for a purpose to be described in greater detail hereinafter.

Figure 6:
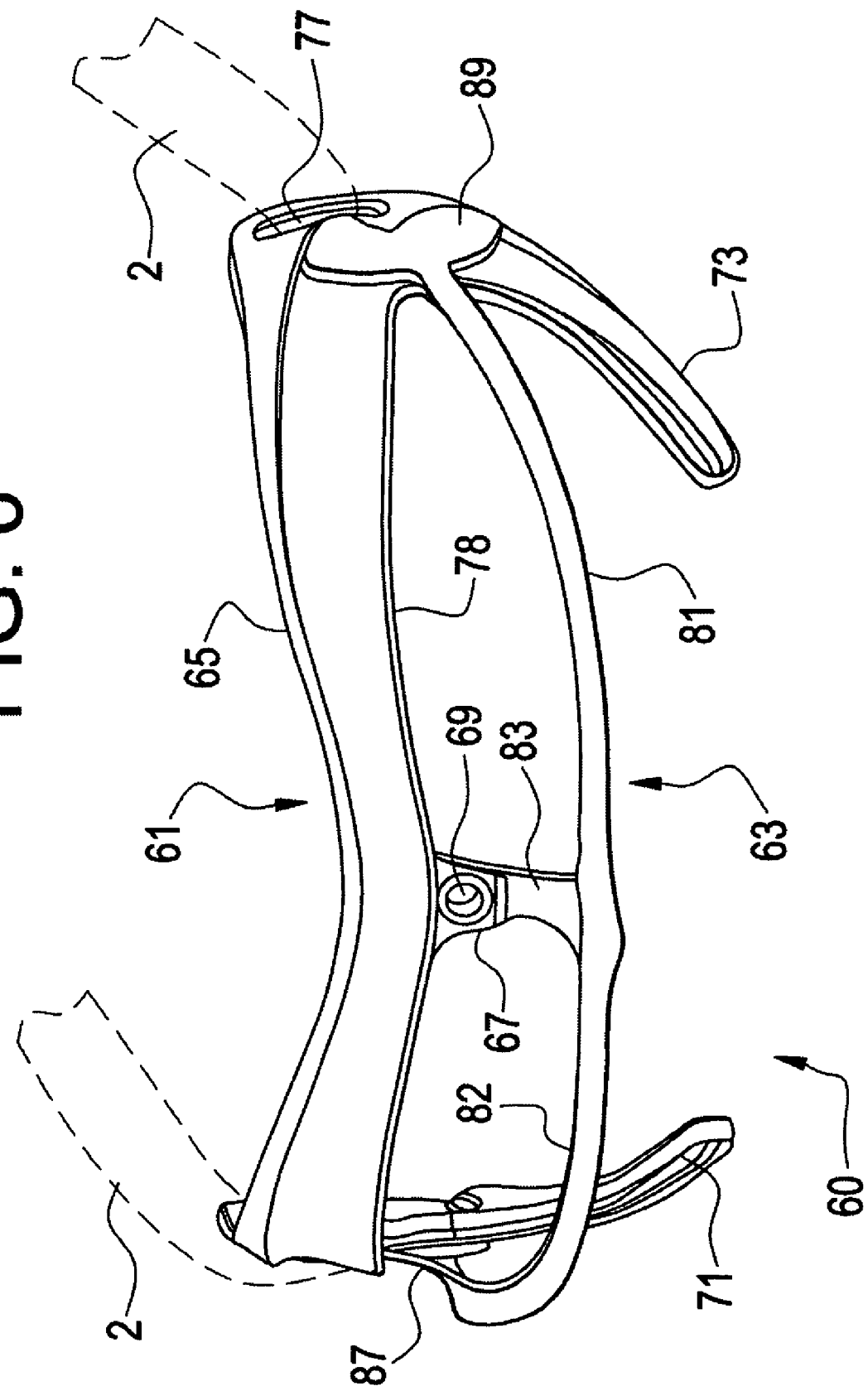
FIG. 6 shows a front perspective view of the preferred embodiment of the present invention.
Figure 13:
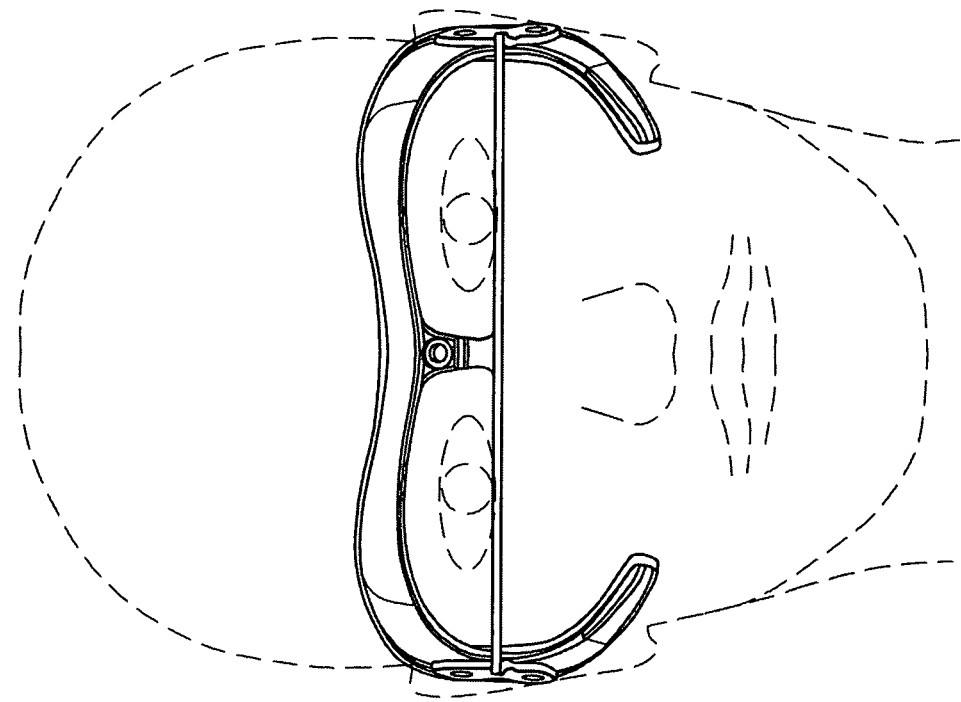
FIG. 13 shows a view similar to that of FIG. 8, but showing the eye protector as worn by a wearer.

With particular reference to FIGS. 6-8, at the peripheral terminations of the elongated portion 65, forwardly and downwardly depending fingers 71 and 73 are provided. With reference to FIGS. 12 and 13, in particular, the fingers 71 and 73 rest on the cheeks of the wearer and act as a limit stop, preventing the eye protector 60 from pivoting downwardly when a lacrosse ball impacts it. In more detail, with the fingers 71 and 73 resting on the cheeks of the wearer, when a lacrosse ball impacts the eye protector 60, there may be a tendency for it to pivot downwardly, thereby exposing the wearer to injury. Engagement of the fingers 71 and 73 with the wearer's cheeks precludes such pivoting movement. At the location where the fingers 71 and 73 emanate from the curved portion 65 of the plastic part 61, slots 75, 77 are provided (FIGS. 6 and 7) to receive the ends of a strap 2 (shown in phantom in FIG. 6) designed to extend around the rear of the head of the wearer to hold the eye protector 60 in mounted position.

With reference to FIGS. 6-11, in particular, the metallic part 63 includes a flat arcuate portion 81 as well as a central tab 83 bent upwardly and including an opening 85 (FIG. 10) aligned with the opening 69 in the tab 67 so that a rivet or other suitable fastener may be fastened through the openings 69 and 85 to fasten the metallic part 63 to the plastic part 61 in a central connection location. Aligned with the central tab 83 is a nose bump 86 best seen in FIG. 9. As seen in FIG. 9, the nose bump 86 emanates from the flat forward edge 88 of the curved portion 81 of the metallic part 63, and curves outwardly and then back.

With particular reference to FIGS. 7 and 14, the metallic part 63 also includes, at the lateral termini of the arcuate portion 81 thereof, wing-shaped attachment members 87 and 89. With particular reference to FIGS. 7 and 14, each member 87, 89 includes holes 91 therethrough that align with holes (not shown) in the plastic part 61 to facilitate attachment at those locations by virtue of suitable attachment members such as, for example, rivets.

The present invention is specifically designed to deflect an incoming lacrosse ball as opposed to blocking it and sending it back toward its point of origin. In order to accomplish this, with specific reference to FIGS. 9 and 15, the curved portion 81 of the metallic part 63 is significantly staggered forwardly with respect to the forward facing leading edge 78 of the curved portion 65 of the plastic part 61. FIGS. 9 and 15, in particular, show the flat rear edge 82 of the curved portion 81 of the metallic part 63 and its relationship to the forward facing leading edge 78 of the curved portion 65 of the plastic part 61. This spacing or horizontal stagger is designated by the reference letter "x" in FIG. 9 and is preferably in the range of ½ to ⅝ inch.

With reference to FIG. 7, another critical dimension is the vertical spacing between the forward edge 78 of the curved portion 65 of the plastic part 61 and the top surface 84 of the curved portion 81 of the metallic part 63. This dimension is depicted in FIG. 7 using the reference letter "y" and is preferably on the order of 1.1 inch±3/16 inch. These dimensions need be compared with the resting dimensions of a lacrosse ball which as described above are 2.47 to 2.55 inches in diameter.

Figure 5:
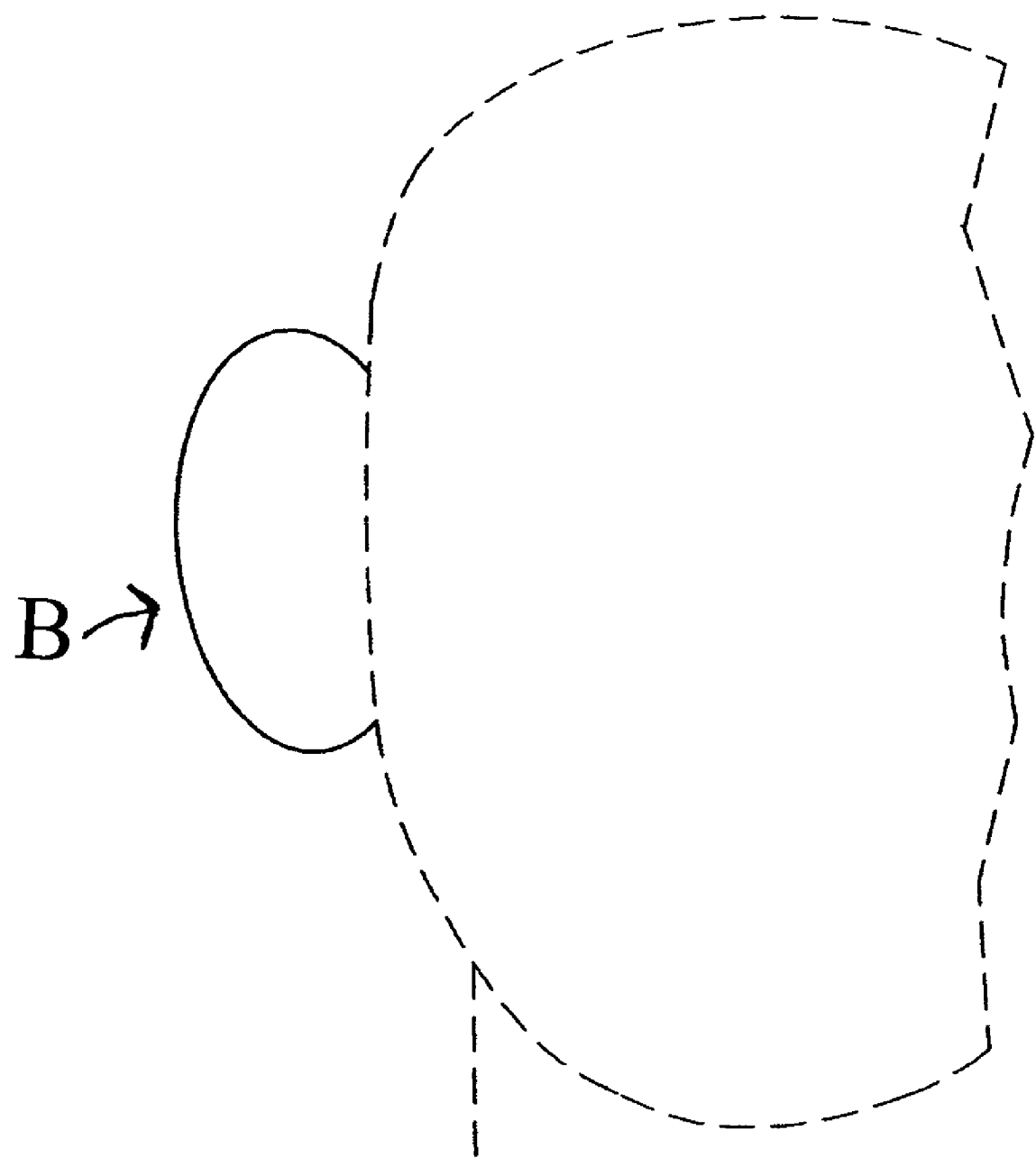
FIG. 5 shows the distortion of a spherical lacrosse ball on impact.

As explained above and with reference to FIG. 5, although a lacrosse ball at rest is spherical, upon impact, it does change shape dramatically. The opening spacing defined by critical dimensions "x" and "y" is designed, within the stated tolerances, to absolutely preclude the forward surface of a lacrosse ball to engage the wearer's eyes under any circumstances while facilitating substantially unobstructed vision.

As best seen in FIGS. 7 and 14, the forward edge 78 of the plastic part 61 and the thinness of the metallic part 63 provide extremely thin surfaces for engagement of an impacting lacrosse ball. FIG. 7 also shows the angled ramp-like surface 74 rearward of the forward edge 78 of the curved portion 65 of the plastic part 61. Looking first at the metallic part 63 and with particular reference to FIGS. 7 and 14, it should be understood that unless a lacrosse ball impacts the forward edge 88 of the metallic part 63 or the nose bump 86 emanating from the forward edge 88 in an orientation in which equal portions of the lacrosse ball are above and below the point of impact, the result will be deflection of the lacrosse ball up or down rather than rebounding toward the point of origin. The same phenomenon occurs with respect to the edge 78 of the plastic part 61. It should be noted that, given the critical dimension "y" which is typically less than half the diameter of the lacrosse ball, virtually every impact on the edge 78 will result in deflection of the ball onto the ramp-like surface 74 and over the head of the wearer. Where the edge 78 is not impacted because the impact is lower, instead, the impact will be on the forward edge 88 or nose bump 86 of the curved portion 81 of the metallic part 63. Such deflections will typically be either upward over the ramp surface 74 or downward and away from the wearer.

Figure 10:
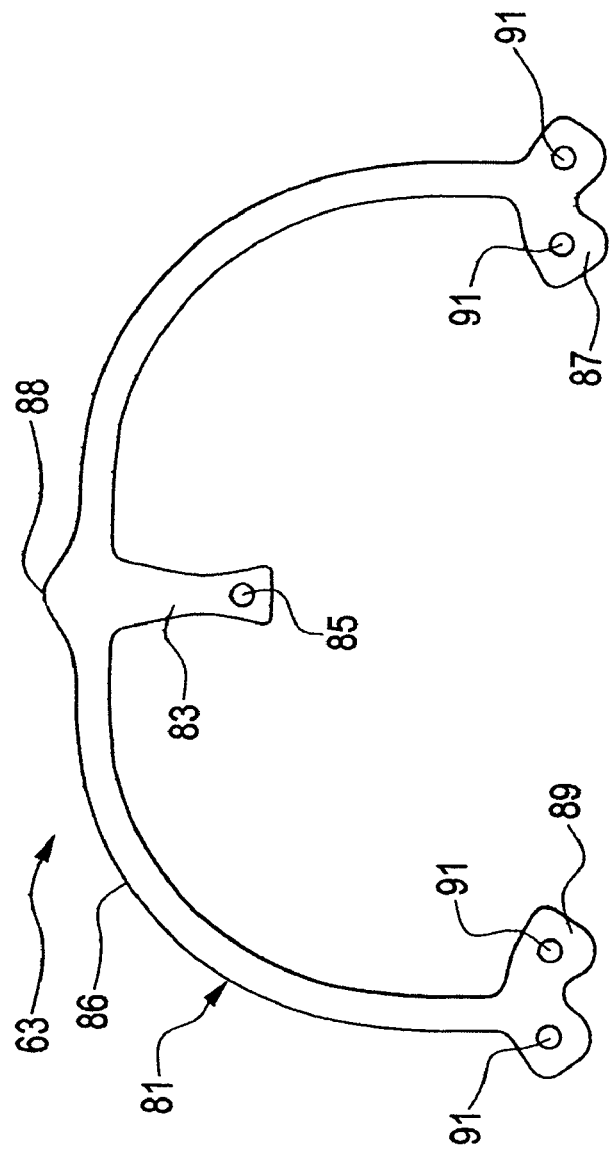
FIG. 10 shows a top view of the metallic part of the present invention as fabricated and before being bent into its installed configuration.
Figure 11:
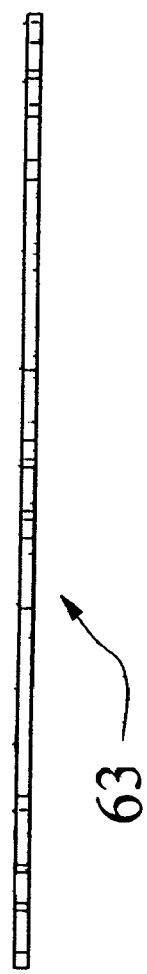
FIG. 11 shows a front view of the device shown in FIG. 10.

With reference to FIG. 10, the fabrication of the metallic part 63 will be better understood. The metallic part 63 is fabricated from a flat sheet stock of the desired metallic material such as, for example, aluminum, stainless steel or other lightweight strong metal such as steel. FIG. 10 shows the metallic part 63 after it has been cut out of the sheet stock by any suitable method such as, for example, use of a computerized water jet cutting mechanism. From the configuration shown in FIG. 10, the central tab 83 is bent upwardly to the configuration shown in particular in FIG. 7, and the peripheral ends just before the wing-shaped attachment members are twisted as particularly shown in FIG. 7 to facilitate attachment to the sides of the plastic part 61. FIG. 11 shows the extreme thinness of the metallic part 63.

In the preferred embodiment of the present invention, the plastic part 61 is made of any desired plastic material fabricated using any desired technique. The metallic part 63 is preferably made of stainless steel or aluminum consisting of a sheet of such material from which the metallic part 63 is cut and then bent into the desired configuration. Alternatively, one or both of the parts may be made of carbon fiber or KEVLAR molded or otherwise fabricated.

As explained above, by staggering the curved portion 81 of the metallic part 63 forward with respect to the forward edge 78 of the curved portion 65 of the plastic part 61, with the stagger being a prescribed distance, and with the top surface 84 of the curved portion 81 of the metallic part 63 being spaced a prescribed distance "y" below the forward edge 78 of the curved portion 65 of the plastic part 61, enhanced performance results, including, crucially, deflection of an incoming lacrosse ball as opposed to the prior art which blocks and repels the lacrosse ball. This is a significant improvement over the prior art because, by deflecting the lacrosse ball, the forces imposed on the face of the wearer are significantly reduced and safety is significantly enhanced.

Figure 16:
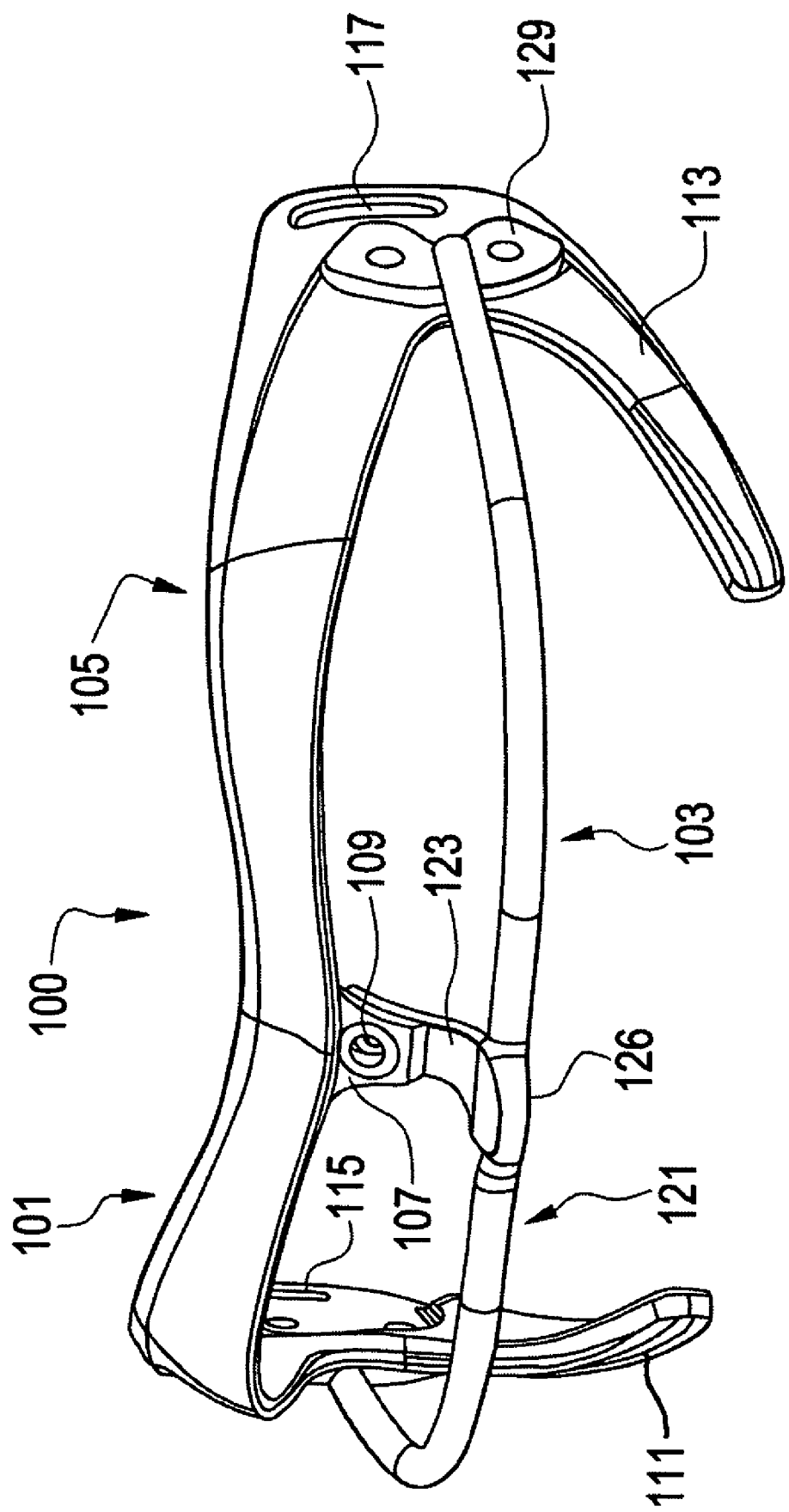
FIG. 16 shows a front perspective view of a second embodiment of the present invention.

With reference to FIGS. 16-18, a second embodiment of the present invention is generally designated by the reference numeral 100 and is seen to include a plastic part 101 and a metallic part 103. The plastic part 101 includes a laterally elongated arcuate portion 105 configured to overlie the eyebrows of the wearer as seen in FIG. 12 with respect to the first embodiment, and curves rearwardly toward the ears of the wearer, as also understood from FIG. 12.

Centrally located on the elongated portion 105 is a downwardly depending central tab 107 having an opening 109 therethrough for a purpose to be described in greater detail hereinafter.

Corresponding to the plastic part 61 of the first embodiment, the plastic part 101 has peripheral terminations of its elongated portion 105 from which forwardly depend fingers 111 and 113. The fingers 111 and 113 rest on the cheeks of the wearer as seen with reference to FIGS. 12 and 13 and the fingers 71 and 73 of the first embodiment. As is the case in the first embodiment, the fingers 111 and 113 prevent the eye protector 100 from pivoting downwardly when a lacrosse ball impacts on it. Engagement of the fingers 111 and 113 on the cheeks of the wearer precludes this pivoting movement. At the intersection of the fingers 111, 113 and the curved portion 105, slots 115 and 117 are provided (FIGS. 16 and 17 in particular) to receive the ends of a strap (shown in FIG. 6) designed to extend around the rear of the head of the wearer to hold the eye protector 100 in mounted position, and a forward facing edge 118.

With reference to FIGS. 16-18, the metallic part 103 includes an arcuate portion 121 as well as a central tab 123 bent upwardly and including an opening (not shown) aligned with the opening 109 in the tab 107 of the plastic part 101 so that a rivet or other suitable fastener (not shown) may be fastened through the openings to fasten the metallic part 103 to the plastic part 101.

Aligned with the central tab 123 is a nose bump 126 that emanates from the forward edge 128 of the curved portion 121 of the metallic part 103 and curves outwardly and back in a similar fashion to the nose bump 86 of the metallic part 63 of the first embodiment 60 of eye protector in accordance with the teachings of the present invention.

As seen in FIGS. 16 and 17, the metallic part 103 also includes, at the lateral termini of the arcuate portion 121 thereof, wing-shaped attachment members 127 (FIG. 17) and 129 (FIG. 16). Each of the members 127 and 129 includes holes 131 aligned with holes (not shown) in the plastic part 101 to facilitate attachment at those locations by virtue of suitable attachment members such as, for example, rivets (not shown).

The arcuate portion 121 of the second embodiment 100 corresponds to the arcuate portion 81 of the first embodiment as presenting a forward facing extremely thin structure. The diameter of the tubing or wire forming the arcuate portion 121 preferably corresponds to the thickness of the sheet from which the arcuate portion 81 of the first embodiment is fabricated. The difference is that the arcuate portion 81 presents a curved forward facing surface that is flat, whereas the forward facing surface in the arcuate portion 121 is curved by virtue of the circular cross-section of the wire or tubing from which it is fabricated. As seen in FIG. 16, the forward facing leading edge and rearward facing edge of the curved portion of the metallic part 103 are curved in a direction perpendicular to the direction of lateral extension of the curved portion. The "x" and "y" spacing dimensions identified in FIGS. 7 and 9 illustrating the first embodiment of the present invention are the same in the second embodiment as well as in the third embodiment to be described in greater detail hereinbelow. The materials of construction of the plastic part 101 and metallic part 103 of the second embodiment of the present invention are the same as for the plastic part 61 and metallic part 63, respectively, of the first embodiment of the present invention.

In the manufacture of the second embodiment 100, the plastic part 101 is the same as the plastic part 61 of the first embodiment and is manufactured in the same manner. The metallic part 121 is fabricated from metallic wire tubing, and the central tab 123 and wings 127-129 may constitute separate structures fabricated and then attached to the arcuate portion B21 by any suitable means including welding or they may be fabricated out of the same material compressed, squeezed, and worked in manners well known to those of ordinary skill in the art.

Figure 19:
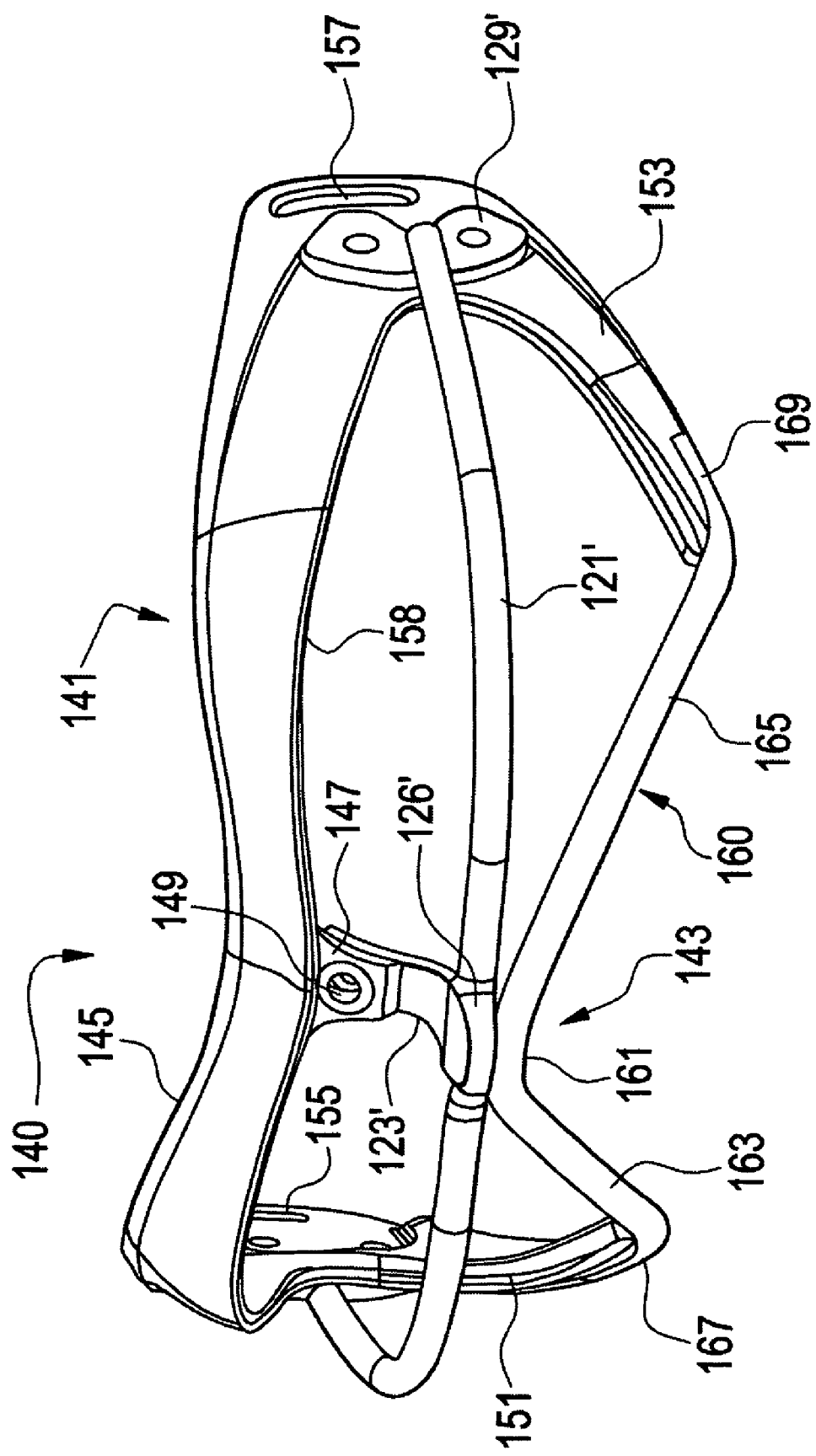
FIG. 19 shows a front side perspective view of a third embodiment of the present invention.

With reference now to FIGS. 19-21, a third embodiment of the present invention is generally designated by the reference numeral 140 and is seen to include a plastic part 141 and a metallic part 143. The plastic part 141 is the same as the plastic parts 61 and 101 described above, and includes a laterally elongated arcuate portion 145, downwardly depending central tab 147 with an opening 149, forwardly depending fingers 151 and 153, slots 155 and 157 to receive a strap, and a forward facing edge 158.

The metallic part 143 includes several structures in common with the metallic part 103 and those structures are depicted using like primed reference numerals. The third embodiment differs from the second embodiment as including an inverted V-shaped metallic tube or wire 160 having a nose bump 161 connected to the nose bump 126' and including a central apex at the nose bump 161 and two downwardly angled legs 163 and 165 having respective terminations 167 and 169 that affix to the ends of the fingers 151 and 153 of the plastic part 141.

The inverted V-shaped metallic part 160 serves to protect portions of the face below the eyes thereof. In the third embodiment, the "x" and "y" dimensions correspond to the same dimensions in the first and second embodiments of the present invention. The additional tube or wire 160 in the third embodiment adds structural integrity to the inventive eye protector without in any way obscuring or limiting the vision of the wearer.

The materials from which the plastic part 141 is fabricated are the same as for the corresponding structures in the first and second embodiments. The materials from which the metallic part 143 is fabricated correspond to the materials set forth above concerning the metallic part 121 of the second embodiment.

Figure 23:
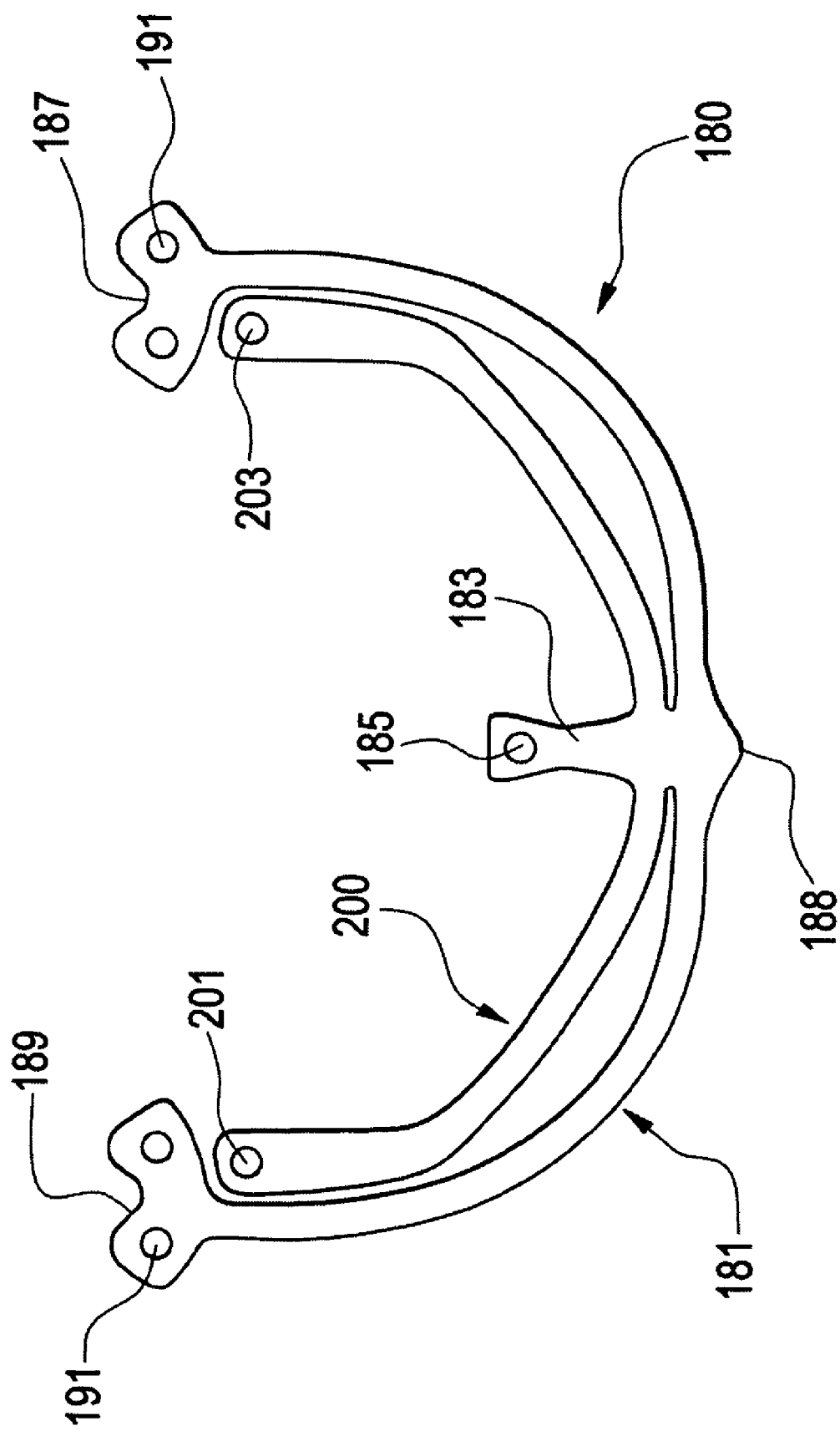
FIG. 23 shows a top view of the metallic part of FIG. 22.

With reference, now, to FIGS. 22 and 23, a modification to the embodiment of FIGS. 19-21 is shown. With reference to FIGS. 22 and 23, in comparison to the embodiment of FIGS. 19-21, the metallic part 121' and the inverted V-shaped metallic tube or wire 160 are replaced with a one piece metallic part 180 fabricated in the same manner as is the metallic part 63. Particular reference is made to FIG. 10 which shows the metallic part 63 of the first embodiment of the present invention as cut out of a flat sheet of metallic material. In this regard, one may compare FIG. 23 with FIG. 10 for the ensuing explanation.

With reference to FIGS. 10 and 23, it is seen that the metallic part 180 includes a flat arcuate portion 181 corresponding to the flat arcuate portion 81, a nose bump 188 corresponding to the nose bump 88, and is integrally formed with a central tab 183 corresponding to the central tab 83, and which includes an opening 185 corresponding to the opening 85.

At the terminations of the flat arcuate portion 181, wing-shaped attachment members 187 and 189 corresponding to the wing-shaped attachment members 87 and 89, respectively, are provided including holes 191 corresponding to the holes 91. In fabrication of the metallic part 180, with reference to FIGS. 22 and 23 as well as FIGS. 6-9, the central tab 183 is bent upward and the hole 185 aligns with the corresponding hole in the plastic part to facilitate connection using any suitable means such as a rivet. The attachment members 187 and 189 are bent at a right angle to the position corresponding to that which is shown in FIGS. 6 and 7 for the members 87 and 89.

Now, comparing FIGS. 22-23 with FIGS. 19-21, it is seen that in correspondence to the inverted V-shaped metallic tube or wire 160, best seen in FIGS. 19 and 21, the metallic part 180 includes a portion 200 that may be bent downward to create a corresponding inverted V-shaped configuration. Holes 201 and 203 at the lateral extremities of the portion 200 facilitate suitable fastening to the plastic part.

The flat arcuate portion 181 has a ratio between its horizontal dimension and its vertical dimension corresponding to that of the flat arcuate portion 81. That ratio is provided for the same purpose as explained above.

The material from which the metallic part 180 is fabricated is the same, including the same alternatives, as those of the metallic part 63.

As explained above, the offsets "x" and "y" are specifically provided to cause an incoming lacrosse ball to deflect away from the inventive eye protector rather than rebounding back toward the source.

The offset of the horizontal members of the eye protector serves to transfer the energy of the ball from a linear force to a rotational force by causing the ball to spin or roll off the structures of the eye protector that it hits. This is a deflecting action versus a blocking action. By deflecting the ball, the likelihood of injury to the eye of the wearer is significantly decreased while at the same time allowing greater visibility to the wearer.

As has been explained above, an eye protector that blocks the ball back toward its source or in that general direction without deflection requires a much more robust construction including the provision of multiple vertical members to prevent the ball from squirting between the horizontal members. These additional vertical members, as explained above, cause obstructions to the visual field.

It is also important to note that the elongated portion 65, 105, 145 of the embodiments of the plastic part of the present invention being made from a composite thermoplastic blend that is both stiff and pliable, flexes downward on impact to momentarily decrease the spacing between the horizontal structures to further preclude ball intrusion into the eye of the wearer.

Accordingly, an invention has been disclosed in terms of preferred embodiments thereof which fulfill each and every one of the objects of the invention as set forth hereinabove, and provide new and useful embodiments of an eye protector of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. An eye protector, comprising:
   a) a first part having a laterally elongated portion including a first forward facing leading edge extending laterally across a forehead of a wearer above and forward of their eyes, said first part further including forwardly downwardly extending fingers extending from peripheral terminations of said laterally elongated portion, said fingers engaging cheeks of a wearer to deter pivoting of said eye protector;
   b) a second part connected to said first part at a central connection location comprising a downwardly depending tab on said first part coupled to an upwardly extending tab on said second part, said second part comprising a one piece thin substantially flat curved portion extending laterally, below and forward of said first forward facing leading edge of said first part, said one piece thin substantially flat curved portion including a second forward facing leading edge, a rearward facing edge, and a flat upper surface therebetween;
   c) said rearward facing edge and said first forward facing leading edge defining therebetween an opening spacing sized to facilitate vision while protecting a wearer's eyes from impact from a projectile, said opening spacing being defined by a horizontal stagger between said rearward facing edge and a vertical projection of said first forward facing leading edge, and a vertical spacing defined between said surface and a horizontal projection of said first forward facing leading edge.

2. The eye protector of claim 1, wherein said first part includes a ramp-like surface extending upwardly and rearwardly with respect to said first forward facing leading edge.

3. The eye protector of claim 1, wherein said thin curved portion of said second part is made from a flat piece of material and said second forward facing leading edge is flat.

4. The eye protector of claim 3, wherein said rearward facing edge is flat.

5. The eye protector of claim 1, wherein said first part is made of plastic.

6. The eye protector of claim 5, wherein said second part is made of metal.

7. The eye protector of claim 1, wherein said second part is made of metal.

8. The eye protector of claim 1, wherein said horizontal stagger is ½ to ⅝ inches.

9. The eye protector of claim 8, wherein said vertical spacing is 1.1 inches±3/16 inch.

10. The eye protector of claim 1, wherein said vertical spacing is 1.1 inches±3/16 inch.

11. The eye protector of claim 1, wherein said surface is arcuate.

12. The eye protector of claim 11, further including an inverted V-shaped member attached below said second part with an apex attached at said central connection location and side terminations connected to said fingers.

13. An eye protector, comprising:
  a) a first part made of plastic and having a laterally elongated portion including a first forward facing leading edge extending laterally across a forehead of a wearer above and forward of their eyes, said first part including a ramp-like surface extending upwardly and rearwardly with respect to said first forward facing leading edge, said first part further including forwardly downwardly extended fingers extending from peripheral terminations of said laterally elongated portion;
  b) a second part made of metal and connected to said first part with a downwardly depending tab on said first part coupled to an upwardly extending tab on said second part and at opposed side connection locations, said second part including a thin curved portion extending laterally below and forward of said first forward facing leading edge of said first part, said thin curved portion including a second forward facing leading edge, a rearward facing edge, and a surface therebetween;
  c) said rearward facing edge and said first forward facing leading edge defining therebetween an opening spacing sized to facilitate vision while protecting a wearer's eyes from impact from a projectile, said opening spacing being defined by a horizontal stagger between said rearward facing edge and a vertical projection of said first forward facing leading edge, and a vertical spacing defined between said surface and a horizontal projection of said first forward facing leading edge.

14. The eye protector of claim 13, wherein said horizontal stagger is ½ to ⅝ inches.

15. The eye protector of claim 14, wherein said vertical spacing is 1.1 inches±3/16 inch.

16. The eye protector of claim 15, wherein said member is tubular.

17. The eye protector of claim 15, wherein said member is flat in cross-section.

18. The eye protector of claim 13, further including an inverted V-shaped member attached below said second part with an apex attached at said central connection location and side terminations connected to said fingers.

19. An eye protector, comprising:
  a) a first part having a laterally elongated portion including a first forward facing leading edge extending laterally across a forehead of a wearer above and forward of their eyes, said first part further including forwardly downwardly extended fingers extending from peripheral terminations of said laterally elongated portion;
  b) a second part connected to said first part, said second part including a thin curved portion extending laterally below and forward of said first forward facing leading edge of said first part, said thin curved portion including a second forward facing leading edge, a rearward facing edge, and a surface therebetween, said thin curved portion of said second part being made from a wire or tube and said second forward facing leading edge and rearward facing edge being curved in a direction perpendicular to the lateral extension of said curved portion;
  c) said rearward facing edge and said first forward facing leading edge defining therebetween an opening spacing sized to facilitate vision while protecting a wearer's eyes from impact from a projectile, said opening spacing being defined by a horizontal stagger between said rearward facing edge and a vertical projection of said first forward facing leading edge, and a vertical spacing defined between said surface and a horizontal projection of said first forward facing leading edge;
  d) said eye protector further including an inverted V-shaped member attached below said second part with an apex attached at said central connection location and side terminations connected to said fingers.

20. The eye protector of claim 19, wherein said member is tubular.

21. The eye protector of claim 19, wherein said member is flat in cross-section.

22. An eye protector, comprising:
  a) a first part having a laterally elongated portion including a first forward facing leading edge extending laterally across a forehead of a wearer above and forward of their eyes;
  b) a second part connected to said first part, said second part comprising a one piece thin substantially flat curved portion extending laterally, below and forward of said first forward facing leading edge of said first part, said one piece thin substantially flat curved portion including a second forward facing leading edge, a rearward facing edge, and a flat upper surface therebetween, said second part being connected to said first part at a central connection location comprising a downwardly depending tab on said first part coupled to an upwardly extending tab on said second part;
  c) said rearward facing edge and said first forward facing leading edge defining therebetween an opening spacing sized to facilitate vision while protecting a wearer's eyes from impact from a projectile, said opening spacing being defined by a horizontal stagger between said rearward facing edge and a vertical projection of said first forward facing leading edge, and a vertical spacing defined between said surface and a horizontal projection of said first forward facing leading edge.

23. An eye protector, comprising:
  a) a first part having a laterally elongated portion including a first forward facing leading edge extending laterally across a forehead of a wearer above and forward of their eyes, forwardly downwardly extended fingers extending from peripheral terminations of said laterally elongated portion;
  b) a second part connected to said first part, said second part comprising a one piece thin substantially flat curved portion extending laterally, below and forward of said first forward facing leading edge of said first part, said one piece thin substantially flat curved portion including a second forward facing leading edge, a rearward facing edge, and an arcuate surface therebetween;
  c) said rearward facing edge and said first forward facing leading edge defining therebetween an opening spacing sized to facilitate vision while protecting a wearer's eyes from impact from a projectile, said opening spacing being defined by a horizontal stagger between said rearward facing edge and a vertical projection of said first forward facing leading edge, and a vertical spacing defined between said surface and a horizontal projection of said first forward facing leading edge;

d) said eye protector further including an inverted V-shaped member attached below said second part with an apex attached at said central connection location and side terminations connected to said fingers.

24. An eye protector, comprising:

a) a first part having a laterally elongated portion including a first forward facing leading edge extending laterally across a forehead of a wearer above and forward of their eyes, said first part further including forwardly downwardly extending fingers extending from peripheral terminations of said laterally elongated portion, said fingers engaging cheeks of a wearer to deter pivoting of said eye protector;

b) a second part connected to said first part, said second part comprising a one piece thin substantially flat curved portion extending laterally, below and forward of said first forward facing leading edge of said first part, said one piece thin substantially flat curved portion including a second forward facing leading edge, a rearward facing edge, and a flat upper surface therebetween;

c) said rearward facing edge and said first forward facing leading edge defining therebetween an opening spacing sized to facilitate vision while protecting a wearer's eyes from impact from a projectile, said opening spacing being defined by a horizontal stagger between said rearward facing edge and a vertical projection of said first forward facing leading edge, and a vertical spacing defined between said surface and a horizontal projection of said first forward facing leading edge; and d) an inverted V-shaped member attached below said second part with an apex attached at said central connection location and side terminations connected to said fingers.

* * * * *

UNITED STATES PATENT AND TRADEMARK OFFICE
CERTIFICATE OF CORRECTION

PATENT NO.       : 8,220,069 B2
APPLICATION NO.  : 12/585908
DATED            : July 17, 2012
INVENTOR(S)      : William H. Brine, III et al.

It is certified that error appears in the above-identified patent and that said Letters Patent is hereby corrected as shown below:

Col. 10, claim 6 should depend upon claim 1

Col. 11, claim 7 should depend upon claim 5

Col. 11, claim 9 should depend upon claim 1

Col. 11, claim 10 should depend upon claim 8

Signed and Sealed this
Ninth Day of October, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,220,069 B2 | Page 1 of 1 |
| APPLICATION NO. | : 12/585908 | |
| DATED | : July 17, 2012 | |
| INVENTOR(S) | : William H. Brine, III et al. | |

It is certified that error appears in the above-identified patent and that said Letters Patent is hereby corrected as shown below:

Column 10, line 66 (claim 6, line 1) "claim 5" should read -- claim 1 --.

Column 11, line 1 (claim 7, line 1) "claim 1" should read -- claim 5 --.

Column 11, line 5 (claim 9, line 1) "claim 8" should read -- claim 1 --.

Column 11, line 7 (claim 10, line 1) "claim 1" should read -- claim 8 --.

This certificate supersedes the Certificate of Correction issued October 9, 2012.

Signed and Sealed this
Sixth Day of November, 2012

David J. Kappos
*Director of the United States Patent and Trademark Office*